(12) United States Patent
McDougall

(10) Patent No.: US 6,421,865 B1  
(45) Date of Patent: Jul. 23, 2002

(54) ELECTRIC TOOTHBRUSH

(76) Inventor: Gregory John McDougall, 10-A Taichi Court, 132 Austin Road, Tsim Sha Tsui, Kowloon (HK)

( * ) Notice: Subject to any disclaimer, the term of this patent is extended or adjusted under 35 U.S.C. 154(b) by 18 days.

(21) Appl. No.: 09/695,896

(22) Filed: Oct. 25, 2000

(51) Int. Cl.[7] ............................................. A61C 17/22
(52) U.S. Cl. ....................................................... 15/22.1
(58) Field of Search ......................................... 15/22.1

(56) References Cited

U.S. PATENT DOCUMENTS

| | | | | |
|---|---|---|---|---|
| 1,703,642 A | * | 9/1929 | Sticht ....................... | 15/22.1 X |
| 3,667,454 A | * | 6/1972 | Prince ...................... | 15/22.1 X |
| 3,685,080 A | * | 8/1972 | Hubner ..................... | 15/22.1 |
| 5,651,157 A | * | 7/1997 | Hahn ........................ | 15/22.1 |
| 5,706,542 A | * | 1/1998 | Okada ....................... | 15/22.1 |
| 5,987,681 A | * | 11/1999 | Hahn et al. ................ | 15/22.1 |
| 6,092,252 A | * | 7/2000 | Fischer et al. ............ | 15/22.1 |

* cited by examiner

*Primary Examiner*—Mark Spisich  
(74) *Attorney, Agent, or Firm*—Jackson Walker L.L.P.

(57) ABSTRACT

An electric toothbrush has an eccentric unbalanced drive shaft extension constrained by a brush head to rotate freely about a longitudinal axis inside a cavity in the brush head. The shaft extension and the brush head are flexibly coupled to a drive shaft and a remote end of a shank, respectively. When the shaft is rotated by an electric motor in a handle of the toothbrush, the brush head is caused to vibrate. The handle is not caused to vibration to any significant extent.

7 Claims, 1 Drawing Sheet

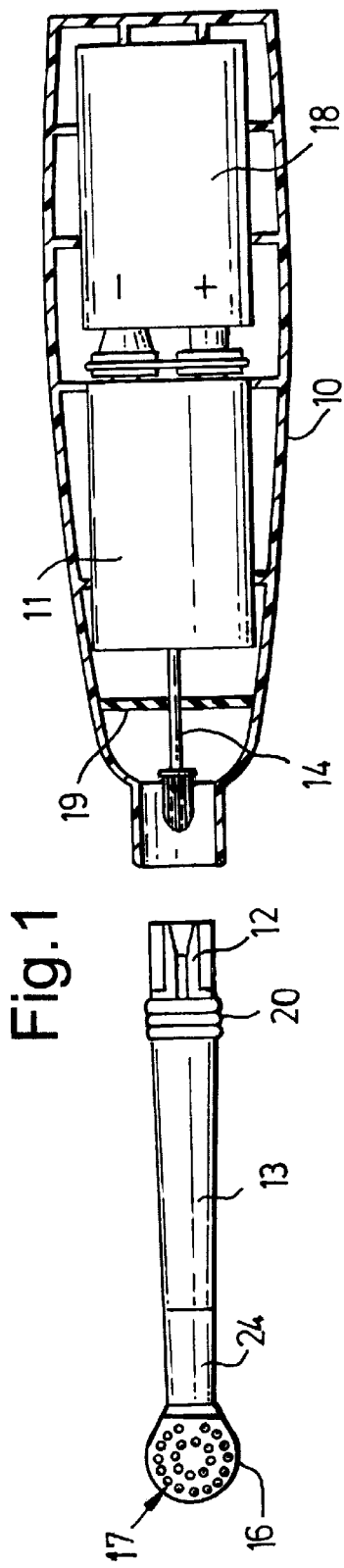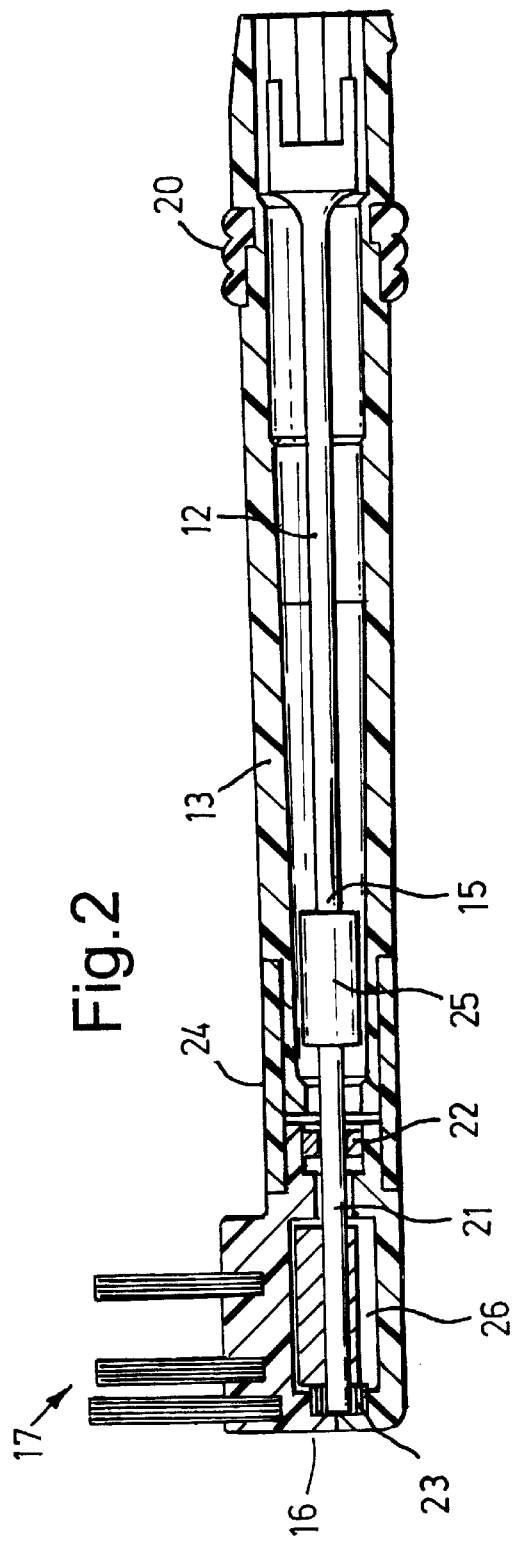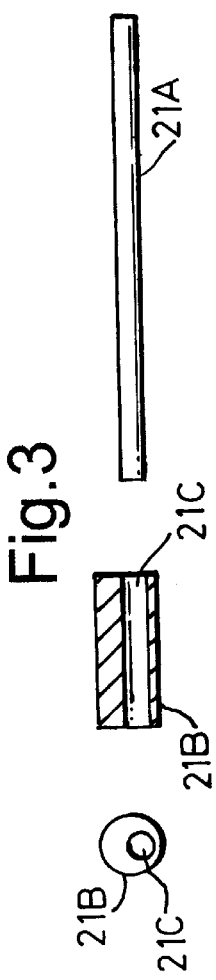

ELECTRIC TOOTHBRUSH

BACKGROUND OF THE INVENTION

1. Field of the Invention

The invention relates to electric toothbrushes.

2. Description of Prior Art

Many toothbrushes are known and widely used having a set of bristles mounted to a brush head that is driven by an electric motor inside a toothbrush handle. The motor may be powered by a battery, also inside the handle, or from a power supply socket adjacent a point-of-use. As such, the brush head can be rotated and/or vibrated by the motor to enhance the operation of the toothbrush for cleaning teeth. For vibrating the brush head, it is already known to provide an eccentrically mounted weight inside the handle directly coupled to the motor. As a result the handle is vibrated and this vibration is transmitted to the brush head in use via a shank of the toothbrush. This means that the user's hand is vibrated. Inherently the vibrations are dampened by the user's grip. When using the toothbrush, the handle vibrations are not comfortable for the user and waste, in effect, considerable mechanical energy that must be supplied by the motor.

SUMMARY OF THE INVENTION

It is an object of the invention to overcome or to at least reduce this problem.

According to the invention there is provided an electric toothbrush having an elongate handle, an electric motor inside the handle, a drive shaft rotatable about a longitudinal axis of the toothbrush inside an elongate shank, a brush head mounted at a remote end of the shank carrying bristles extending general transversely to the longitudinal axis from the brush head, an eccentrically unbalanced drive shaft extension that is constrained by the brush head to be freely rotatable within a cavity in the brush head about said longitudinal axis, in which the brush head and the shaft extension are flexibly coupled to the remote end of the shank and to the drive shaft, respectively, such that when the drive shaft is rotated the brush head is caused to vibrate relative to the shank.

The drive shaft extension may be constrained by at least one bearing in the brush head that is positioned about said longitudinal axis.

The shaft extension may comprises a shaft rotatable about the longitudinal axis and a sleeve that fits over the shaft having an off-centre channel in which the extension shaft fits. The sleeve is preferably made of metal.

A resilient bush may be arranged to hold and connect the brush head to the remote end of the shank. The brush may be formed by over-molding resilient material over and form connection between the brush head and the remote end of the shank.

A resilient tube may be used to drivingly connect the shaft extension to the drive shaft.

Preferably, the drive shaft is driven at between 10000 and 12000 revolutions pre minute.

BRIEF DESCRIPTION OF THE DRAWINGS

An electric toothbrush according the invention will now be described with reference to the accompanying drawings in which:

FIG. 1 is an exploded part-sectioned plan view of the toothbrush;

FIG. 2 is a sectioned side view of part of the toothbrush; and

FIG. 3 show views of components of the brush that form a shaft extension.

DESCRIPTION OF THE PREFERRED EMBODIMENT

Referring to the drawings, in FIG. 1 the toothbrush has an elongate handle 10 and a motor 11 mounted inside the handle. A drive shaft rotatable about a longitudinal axis of the toothbrush inside a shank 13, is releasably coupled in use at one end to a rotor 14 of the motor. A remote end 15 of the drive shaft is connected, as described below, to a brush head 16 that has a set of bristles 17 extending from the brush head in a direction generally transverse to the said longitudinal axis. A battery pack 18 inside the handle provides power for the motor 11. One rubber seal 19 is mounted inside the handle and another rubber seal 20 is provided to seal and connect the shank 13 to the handle 10.

In FIG. 2, the remote end 15 of the drive shaft is rotationally gripped by a resilient tube 25 that fits to a drive shaft extension 21. The shaft extension is rotatably supported by two bearings 22 and 23 provided in the brush head 16. The brush head 16 is flexibly connected to a remote end of the shank 13 by a resilient bush 24. The bush 24 may be formed by an over-molding of suitable flexible plastics material.

The drive shaft extension 21 is formed of two components (see FIG. 3), that comprise a metal shaft 21A and a metal sleeve 21B that has an off-centre channel 21C in which the shaft 21A fits. As such the drive shaft extension forms an eccentrically unbalanced component that is constrained by the bearings 22 and 23 to rotate freely inside a cavity formed in the brush head. As a result, when the drive shaft 12 rotates the brush head 16 is caused to vibrate relative to the shank 13. Importantly, these vibrations are not transferred, to any major extent, along the shank to the handle 10 so that the toothbrush is comfortable to use. Also, the effective energy required to generate the vibrations is significantly less than in prior art arrangements where vibrations are generated inside the handle and transferred by the shank to the brush head. As explained earlier, a major energy disadvantage in the prior art is that the user inherently dampens the vibrations by gripping the handle quite tightly and so a lot of energy is wasted.

It is generally preferable for creating suitable vibrations in the described embodiment to run the drive shaft 12 at between 10000 and 12000 revolutions per minute.

It is possible to form the eccentric unbalance in many other ways, such as by providing an integrally formed drive shaft extension where the shaft has an uneven weight distribution, as regards the longitudinal axis (or rotational axis) of the shaft extension. In each case, the brush head is required to constrain the drive shaft extension to rotate about the longitudinal axis. In providing this constraint, vibrations are transmitted by the unbalanced shaft extension to act on the brush head and hence vibrate the bristles 17 as required. It will be appreciated that the constraint may be arranged in different ways, and where preferred, a single bearing 23 say, used. A single bearing could be positioned intermediate the length of the shaft extension, if the sleeve 21B is in two parts, one part on either side of the intermediate bearing.

It will be appreciated that the toothbrush may have a single tuft of bristles so that the toothbrush may form and be used an a 'tooth pick'.

The amount of eccentricity and/or the unbalanced weight of the sleeve 21B can be changed to alter the characteristics of the vibrations. In general, the more 'unbalanced' the drive extension, the 'harder' the tooth brushing effect will be. Thus, it is a quite simple matter to arrange for so-called hard, medium, and soft vibration/brushing effects, by using extension shafts with different unbalanced characteristics, and/or driven at different speeds, to suit different user requirements.

I claim:

1. An electric toothbrush having an elongate handle, an electric motor inside the handle, a drive shaft rotatable about a longitudinal axis of the toothbrush inside an elongate shank, a brush head mounted at a remote end of the shank carrying bristles extending general transversely to the longitudinal axis from the brush head, an eccentrically unbalanced drive shaft extension that is constrained by the brush head to be freely rotatable within a cavity in the brush head about said longitudinal axis, in which the brush head and the shaft extension are flexibly coupled to the remote end of the shank and to the drive shaft, respectively, such that when the drive shaft is rotated the brush head is caused to vibrate relative to the shank.

2. An electric toothbrush according to claim 1, in which the drive shaft extension is constrained by at least one bearing in the brush head that is positioned about said longitudinal axis.

3. An electric toothbrush according to claim 1, in which the shaft extension comprises a shaft rotatable about the longitudinal axis and a sleeve that fits over the shaft having an off-centre channel in which the extension shaft fits.

4. An electric toothbrush according to claim 3, in which the sleeve is made of metal.

5. An electric toothbrush according to claim 1, including a resilient bush that holds and connects the brush head to the remote end of the shank.

6. An electric toothbrush according to claim 1, including a resilient tube that drivingly connects the shaft extension to the drive shaft.

7. An electric toothbrush according to claim 1, in which the drive shaft is driven at between 10000 and 12000 revolutions per minute.

* * * * *